US00PP17237P3

(12) United States Plant Patent
Stemkens

(10) Patent No.: US PP17,237 P3
(45) Date of Patent: Nov. 28, 2006

(54) ***SUTERA* PLANT NAMED 'SUTCATRWHI'**

(50) Latin Name: *Sutera diffusa*
Varietal Denomination: Sutcatrwhi

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 168 days.

(21) Appl. No.: 11/000,577

(22) Filed: Dec. 1, 2004

(65) Prior Publication Data

US 2006/0117432 P1 Jun. 1, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,682 P2 * 6/2002 Polman ..... Plt./263 .....

OTHER PUBLICATIONS

UPOV ROM GTITM Computer Database, GTI Jouve Retrieval Software 2005/03 Citations for 'Sutcatrwhi'.*

* cited by examiner

* cited by examiner

*Primary Examiner*—Kent Bell
*Assistant Examiner*—W. C. Haas
(74) *Attorney, Agent, or Firm*—Bruce Vrana

(57) ABSTRACT

A new and distinct variety of *Sutera* plant particularly distinguished by its white flowers, earliness to flower, thick stems, heat tolerance and a growing habit that is spreading and trailing.

1 Drawing Sheet

Latin name of the genus and species of the plant claimed: *Sutera diffusa.*
Varietal denomination: 'Sutcatrwhi'.

BACKGROUND OF THE NEW PLANT

The present invention comprises a new distinct cultivar of *Sutera,* botanically known as *Sutera diffusa.*

The new cultivar is propagated from cuttings resulting from the cross of 'B22' and 'B24'. 'B22' is a white flowering *Sutera* having a spreading, trailing habit. 'B22' is not commercially available and is not known by any synonyms. 'B24' is a white flowering *Sutera* having a compact habit. 'B24' is not commercially available and is not known by any synonyms. Neither 'B22' or 'B24' has been patented.

As a result of this cross the present cultivar was created in 2000 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty is firmly fixed.

This new *Sutera* plant is an annual in most climatical zones in the US, only in zones 9 and 10 it is a perennial plant.

SUMMARY OF THE INVENTION

It was found that the cultivar of the present invention:

a) Exhibits white flowers;

b) has thick stems;

c) exhibits a spreading and trailing growth habit; and d) is very resistant to hot conditions.

DESCRIPTION OF THE DRAWING

This new *Sutera* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Sutera.* The data that define these characteristics were collected from asexual reproductions carried out in Enkhuizen, Netherlands. The plant history was taken on 15 week old plants, blossomed under natural light in a greenhouse and grown in 11 cm containers. Colour readings were taken in the greenhouse under ambient light. Colour references are primarily to The R.H.S. Colour Chart of The Royal Horticultural Society of London.

TABLE 1

Differences between the new cultivar 'Sutcabl', its parents and a similar cultivar

| | 'Sutcabl' | 'B21' | 'B23' | 'Blue Showers' |
|---|---|---|---|---|
| Flower color | Deep Blue | Deep blue | White | Blue |
| Stem thickness | Thick | Medium | Thick | Thin |
| Plant habit | Compact | Trailing | Compact | Trailing |
| Flower size | Medium | Big | Small | Small |

'Bridal Showers' is not patented.

The plant:
*Classification.*—Botanical: *Sutera diffusa.*

*Parentage.*—Female parent: A seedling named 'B22' is one of our seedlings from our B-generation of plants bred in 1999. Pollen parent: A seedling named 'B24' is one of our seedings from our B-generation of plants bred in 1999.
*Growth habit.*—Spreading and trailing, decumbent.
*Plant height.*—14 to 18 cm.
*Spreading area of plant.*—40 to 58 cm.
*Growth rate.*—Rapid growing.
*Strength.*—Good.
*Branching habit.*—Short internodes and on each knot more than two appearing shoots give a plant that is more branched than normal.
*Blooming period.*—From May until November.

The stem:
*Diameter.*—2 to 3 mm.
*Shape.*—Cylindrical.
*Anthocyanin pigmentation.*—Absent.
*Color of the stem.*—137B.
*Length of internode.*—14 to 28 mm, depending on the light where the plant is propagated.
*Pubescence.*—Sparse.

The foliage:
*Phyllotaxis.*—Opposite, decussate.
*Shape of blade.*—Broadly ovate.
*Shape of the blade apex.*—Acute.
*Shape of the blade base.*—Truncate.
*Leaf margin.*—Dentate.
*Venation.*—Pinnate.
*Texture.*—Upper surface: Smooth, glabrous. Lower surface: Slightly pubescent.
*Length.*—14 to 20 mm.
*Width.*—14 to 24 mm.
*Thickness.*—1 to 2 mm.
*Depth of incision.*—Less than 1 mm.
*Color.*—Upper side: N138B. Lower side: 137C.
*Length of petiole.*—1 to 2 mm.
*Diameter of petiole.*—1 mm.
*Color of petiole.*—137B.
*Fragrance.*—Musk.

The bud:
*Pedicel length.*—8 to 11 mm, depending on season.
*Pedicel diameter.*—1 mm.
*Pedicel color.*—137D.
*Pedicel angle.*—About 60 degrees from the stem.
*Bud size.*—Diameter: 1 mm. Length: 4 to 8 mm.
*Bud shape.*—Obovate.
*Bud color.*—155A.
*Sepals.*—Color: 137D. Number: 5. Shape: Erect calyx. Size: 3 mm.
*Shape of sepals.*—Gamopetalous, grown together at the base of the sepal.

The flower:
*Flower diameter.*—15 to 18 mm.
*Flower tube length.*—5 to 8 mm.
*Throat diameter, distal end.*—2 to 4 mm.
*Tube diameter, proximal end.*—1.5 to 2.5 mm.
*Form.*—Salverform.
*Symmetry.*—Radial symmetric.
*Type.*—Solitary, axillary.
*Color.*—Upper surface: Between N155A. Lower surface: N155A.
*Corolla tube.*—Cylindrical.
*Corolla tube color.*—8C.
*Overlapping of petals.*—Separate.
*No. of petals.*—5.
*Shape of the petals.*—Gamopetalous, grown together at the base of the petal, forming a corolla.
*Petal lobe.*—Length: 4 to 6 mm. Width: 2 to 4 mm. Shape: Spatulate. Apex: Rounded. Margin: Entire. Texture: Smooth.
*Calyx.*—Length: 6 to 8 mm. Diameter: 3 mm. Shape: Narrow, linear. Apex: Acute. Margin: Entire.
*Texture of the calyx.*—Upper surface: Pubescent. Lower surface: Pubescent.
*Color of the calyx.*—Upper surface: 137B. Lower surface: 137C.
*Anthocyanin pigmentation of calyx limb.*—Absent.
*Flower fragrance.*—No fragrance detected.
*Lastingness of one flower.*—Flowers stay open 6 to 8 days.

Reproductive organs:
*Number of reproductive organs.*—1 pistil, 4 stamens.
*Pollen production.*—Very low.
*Stigma color.*—138D.
*Stamen color.*—13B.
*Stamen arrangement.*—Didynamous.
*Stamen type.*—Basifixed.
*Dehiscence of stamens.*—Extrorse.
*Ovary position.*—Ovary superior, flower hypogynous.
*Style shape.*—Style terete.
*Style length.*—9 mm.
*Pistil length.*—12 mm.

Seeds: No seedset is observed.

Roots:
*Type of roots.*—Fibrous, fine, color 155A.

Physiological and ecological characteristics: Extreme tolerance to heat is observed.

Propagation: Propagation is done by axillary cuttings.

Tips of stems are used, which take 6 days to initiate roots and 12 days to develop roots.

What is claimed is:

1. A new and distinct variety of *Sutera* plant named 'Sutcatrwhi', substantially as illustrated and described herein.

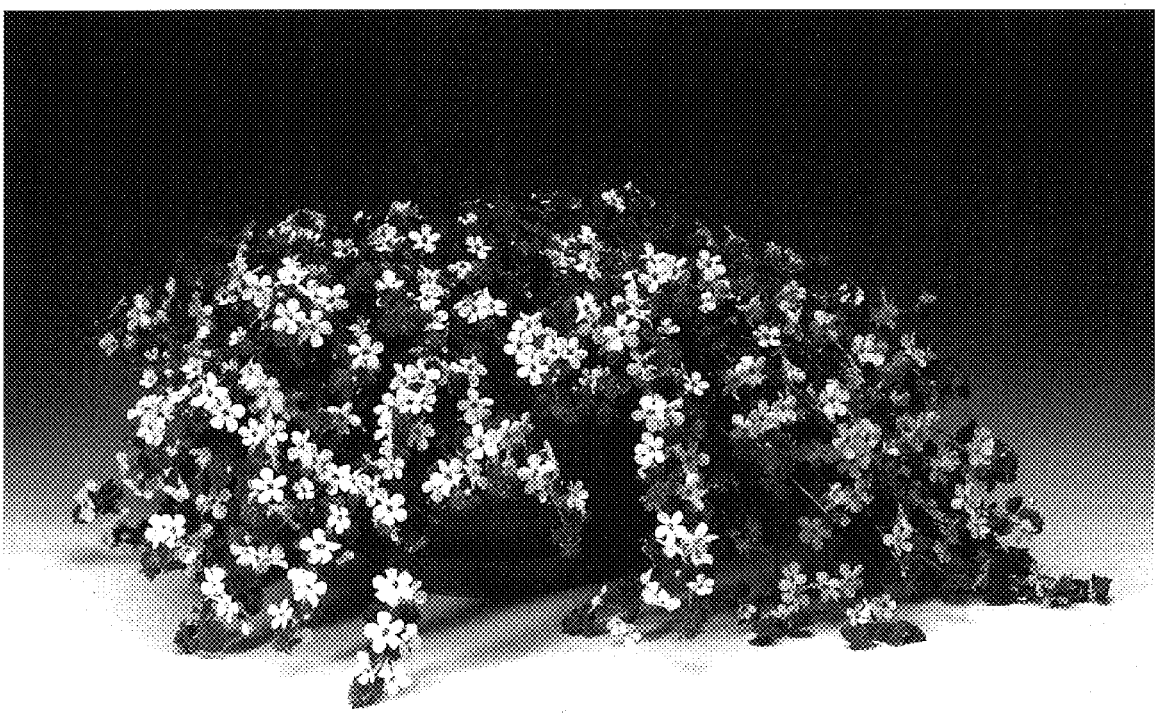

* * * * *